United States Patent [19]

Aslam et al.

[11] Patent Number: 4,794,205

[45] Date of Patent: Dec. 27, 1988

[54] METHOD FOR PRODUCING ALKENYLTHIOPHENOLS AND THEIR ESTERS

[75] Inventors: Mohammad Aslam; Kenneth G. Davenport, both of Corpus Christi, Tex.

[73] Assignee: Hoechst Celanese Corporation, Somerville, N.J.

[21] Appl. No.: 940,675

[22] Filed: Dec. 10, 1986

[51] Int. Cl.$^4$ .................. C07C 153/11; C07C 148/00
[52] U.S. Cl. ..................................... 558/257; 568/67; 568/68
[58] Field of Search ................... 558/257; 568/67, 68

[56] References Cited

U.S. PATENT DOCUMENTS 3,475,251 10/1969 Widmer .............................. 558/257
3,476,791 11/1969 Newman et al. ..................... 558/257

OTHER PUBLICATIONS

P. A. Schweitzer, *Handbook of Separation Techniques for Chemical Engineers* (McGraw–Hill) pp. 1–386 (one page).
Newman et al., Journal of Organic Chemistry 31, 3980–3984 (1966).
Kwart et al., Journal of Organic Chemistry 31, 410–413 (1966).
Overberger et al., Journal of the American Chemical Society 78, 4792–4797 (1956).
Nuyken et al., Polymer Bulletin 4, 75–82 (1981).
Reid, Organic Chemistry of Bivalent Sulfur, vol. III, Chem. Pub. Co., Ive., N.Y., 1962 pp. 27 & 31.

*Primary Examiner*—Alan L. Rotman
*Assistant Examiner*—Robert C. Whittenbaugh

*Attorney, Agent, or Firm*—Marvin Turken; Donald R. Cassady

[57] ABSTRACT

A method is provided for preparing alkenylthiophenols, e.g., para-vinylthiophenol, or their esters, e.g., para-vinylthiophenol acetate by reacting a hydroxy aromatic ketone, e.g., 4-hydroxyacetophenone (4-HAP) with an N,N-di(organo)thiocarbamoyl halide, e.g., N,N-dimethylthiocarbamoyl chloride (DMTC) to form an O-(acylaryl) N,N-di(organo)thiocarbamate, e.g., O-(4'-acetophenyl) N,N-dimethylthiocarbamate, and pyrolytically rearranging the latter compound to form an S-(acylaryl) N,N-di(organo)thiocarbamate, e.g., S-(4-4--acetophenyl) N,N-dimethylthiocarbamate. In one procedure, the latter compound is directly reduced to form an S-(1-hydroxyalkylaryl) N,N-di(organo) thiocarbamate, e.g., S-[4'-(1-hydroxyethyl)phenyl] N,N-dimethylthiocarbamate, which is either hydrolyzed to form a (1-hydroxyalkyl) thiophenol, e.g., 4'-(1-hydroxyethyl) thiophenol, which optionally after acylation of its thiol group, is dehydrated to form the alkenylthiophenol wherein the double bond is at the ring-bonded carbon atom, e.g., para-vinylthiophenol, or the S-(1-hydroxyalkylaryl) N,N-di(organo) thiocarbamate is dehydrated to form an S-(alkenylaryl) N,N-di(organo) thiocarbamate, e.g., S-(4-vinylphenyl) N,N-dimethylthiocarbamate which is hydrolyzed to form the alkenylthiophenol. In an alternative procedure, the S-(acylaryl) N,N-di(organo)thiocarbamate is hydrolyzed and the resulting thiol acylated with an acylating agent, e.g., acetyl chloride, to produce an acylthiophenol ester, e.g., 4-acetothiophenol acetate, which is then reduced and hydrolyzed to produce the (1-hydroxyalkyl) thiophenol. The latter compound is then dehydrated to produce the alkenylthiophenol, or acylated and dehydrated to produce alkenylthiophenol thioester, as described in the first procedure.

15 Claims, No Drawings

METHOD FOR PRODUCING ALKENYLTHIOPHENOLS AND THEIR ESTERS

BACKGROUND OF THE INVENTION

This invention relates to the production of alkenylthiophenols, e.g., para-vinylthiophenol, and their esters, e.g., para-vinylthiophenol acetate.

Alkenylthiophenols, e.g., para-vinylthiophenol, and their esters, have utility as monomers in the formation of sulfur-containing graft polymers and copolymers having various end uses. For example, alkenylthiophenol esters, e.g., para-vinylthiophenol acetate (or para-vinylphenylthiol acetate), are suitable sulfur-containing monomers for the production of graft copolymers which, after hydrolysis, are useful in the formation of rubber reinforcing elements having superior adhesion to rubber; see for example, U.S. Pat. No. 3,475,251 issued Oct. 28, 1969 to Widmer. These sulfhydryl containing monomers are also suitable for the production of resins useful for the extraction of metals such as mercury and lead; see for example, P.A. Schweitzer, *Handbook of Separation Techniques for Chemical Engineers* (McGraw-Hill), page 1–386 (one page).

Newman et al, Journal of Organic Chemistry 31, 3980-3984 (1966), teach the formation of O-aryl dialkylthiocarbamates by reaction of a phenol with a dialkyl thiocarbamoyl chloride, and the pyrolytic rearrangement of O-aryl dialkylthiocarbamates to S-aryl dialkylthiocarbamates. Specifically disclosed in Table I is the pyrolytic rearrangement of O-(4'-acetophenyl) dimethylthiocarbamate to S-(4'-acetophenyl) dimethylthiocarbamate.

Newman et al, U.S. Pat. No. 3,476,791, disclose a process similar to that disclosed in the article cited in the preceding paragraph and was issued to patentees who are the same as the authors of such article. Example 14 of the patent shows the preparation of p-acetylphenyl dimethylthiolcarbamate from p-acetylphenyl dimethylthioncarbamate.

Kwart et al, Journal of Organic Chemistry 31, 410–413 (1966), show the vapor phase pyrolytic rearrangement of various diaryl thioncarbonates to O,S-diaryl thiolcarbonates and of various O-aryl dialkylthioncarbamates to S-aryl dialkylthiolcarbamates.

Overberger et al, Journal of the American Chemical Society 78, 4792–4797 (1956), teach the preparation of p-vinylphenyl thioacetate by diazotizing p-aminoacetophenone and reacting the diazonium compound with potassium ethyl xanthate to form ethyl p-acetylphenyl xanthate. The latter is reacted with sodium borohydride to yield p-thiol-alpha-methylbenzyl alcohol which is converted to the diacetate with acetyl chloride. The diacetate is then cracked at 460° C to yield the p-vinylphenyl thioacetate.

Nuyken et al, Polymer Bulletin 4, 75–82 (1981) disclose the preparation of 4-vinylbenzenethiol by a method similar to that taught by Overberger et al discussed previously except that the 4-(1-hydroxyethyl)-benzenethiol, i.e., the p-thiol-alpha-methylbenzyl alcohol, is dehydrated directly at 300° C. using alumina as catalyst to form the 4-vinylbenzenethiol.

The diazonium compounds and xanthates formed during the methods described by Overberger et al and Nuyken et al give rise to explosive hazards and thus may render such methods undesirable.

SUMMARY OF THE INVENTION

In accordance with this invention, alkenylthiophenols wherein the alkenyl double bond is at the ring-bonded carbon atom, e.g., para-vinylthiophenol or para-mercaptostyrene, and their thioesters, are produced by reacting a hydroxy aromatic ketone, e.g., 4-hydroxyacetophenone (4-HAP), with an N,N-di(organo)thiocarbamoyl halide, e.g., N,N-dimethylthiocarbamoyl chloride (DMTC), to form an O-(acylaryl) N,N-di(organo)thiocarbamate, e.g., O-(4'-acetophenyl) N,N-dimethylthiocarbamate, and pyrolytically rearranging the O-(acylaryl) N,N-di(organo)thiocarbamate to form an S-(acylaryl) N,N-di(organo)thiocarbamate, e.g., S-(4'-acetophenyl) N,N-dimethylthiocarbamate. In one procedure, the latter compound is directly reduced to form an S-(1-hydroxyalkylaryl) N,N-di(organo)thiocarbamate, e.g., S-[4'-(1-hydroxyethyl)phenyl]N,N-dimethylthiocarbamate. The latter compound may then be hydrolyzed to form a (1-hydroxyalkyl) thiophenol, e.g., 4'-(1-hydroxyethyl) thiophenol, which, optionally after acylation of its thiol group, is dehydrated to form the alkenylthiophenol wherein the double bond is at the ring-bonded carbon atom, e.g., para-vinylthiophenol. Note in this connection that for some purposes, e.g., the formation of certain polymers, it is preferable to have the alkenylthiophenol in the form of its thioester, e.g., para-vinylthiophenol acetate. In that case, the thiol group of the (1-hydroxyalkyl) thiophenol is acylated before dehydration, e.g., with acetyl chloride, to form the (1-hydroxyalkyl) thioester, e.g., 4'-(1-hydroxyethyl) thiophenol acetate, which is then dehydrated to obtain the alkenylthiophenol ester. It is also possible to dehydrate the S-(1-hydroxyalkylaryl) N,N-di(organo)thiocarbamate to form an S-(alkenylaryl) N,N-dimethylthiocarbamate, which may then be hydrolyzed to form the alkenylthiophenol. The latter compound may, if desired, be acylated, e.g., with a lower alkanoic acid, to form the alkenylthiophenol ester.

In an alternative procedure, the S-(acylaryl) N,N-di(organo)thiocarbamate is hydrolyzed and the resulting thiol acylated with an acylating agent, e.g., acetyl chloride, to produce a acylthiophenol ester, e.g., 4'-acetothiophenol acetate, which is then reduced and hydrolyzed to produce the (1-hydroxyalkyl) thiophenol. The latter compound is then dehydrated to produce the alkenylthiophenol, or acylated and dehydrated to produce the alkenylthiophenol ester, as described in the first procedure. An advantage of this procedure over that involving the direct reduction of hhe thiocarbamate described previously is that the occurrence of amine impurities resulting from the reaction of the thiocarbamate is minimized or eliminated.

It is preferable although not absolutely necessary that the thiol group of the (1-hydroxyalkyl) thiophenol be masked, i.e., acylated or esterified, with a thiocarbamoyl group or acyl group, as described, before dehydration to the alkenyl compound since this avoids the consumption of one molar equivalent of an expensive hydride such as sodium borohydride, and also has the effect of increasing the volatility of the compound, which is advantageous for subsequent purification. Moreover, as stated, an acylated product is often more useful in polymerization.

The reaction between a hydroxy aromatic ketone and an N,N-di(organo)thiocarbamoyl halide to form an O-(acylaryl) N,N-ii(organo)thiocarbamate is as shown in equation (I):

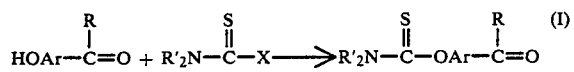

where X is halide, e.g., fluoride, chloride or bromide, Ar is a divalent aromatic radical, and R and R' are monovalent organo radicals as further defined hereinafter.

The pyrolytic rearrangement of the O-(acylaryl) N,N-di(organo)thiocarbamate to the S-(acylaryl) N,N-di(organo)thiocarbamate proceeds as in equation (II):

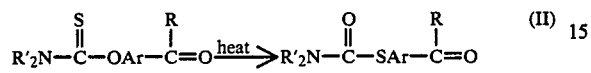

The direct reduction and hydrolysis of the S-(acylaryl) N,N-di(organo)thiocarbamate to form the (1hydroxyalkyl) thiophenol proceeds as in equation (III), wherein "[H]" represents a reducing agent with available hydrogen such as sodium borohydride:

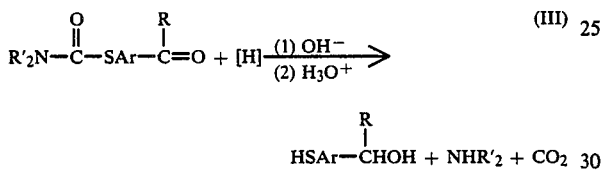

The hydrolysis and acylation of the S-(acylaryl) N,N-di(organo)thiocarbamate to form an acylthiophenol thioester proceeds as in equations (IV) and (V):

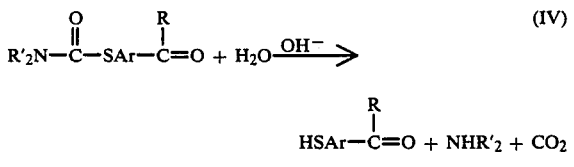

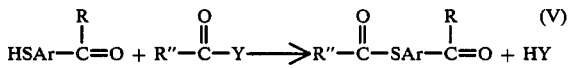

where R" and Y are as hereinafter defined.

The reduction and hydrolysis of the acylthiophenol ester to form a (1hydroxyalkyl) thiophenol proceeds as in equation (VI):

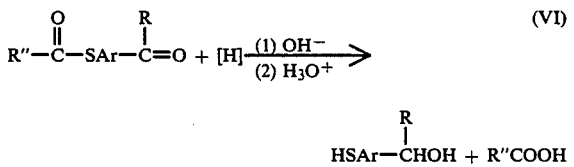

The acylation of the (1-hydroxyalkyl) thiophenol to its thioester proceeds as in equation (VII):

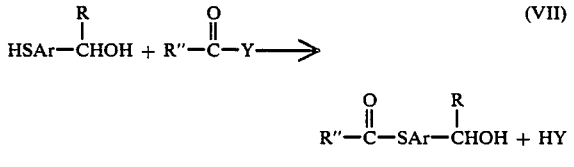

The dehydration of the (1-hydroxyalkyl) thiophenol ester to form an alkenylthiophenol ester proceeds as in equation (VIII):

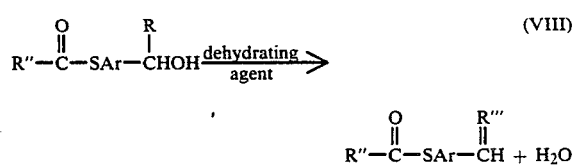

where R''' is a divalent alkylidene group as hereinafter defined.

The dehydration of the free (1-hydroxyalkyl) thiophenol to form the alkenylthiophenol proceeds as in equation (IX):

In the foregoing equations, Ar is a divalent phenylene or naphthylene radical resulting from the removal of two ring hydrogen atoms from benzene or naphthalene, either unsubstituted or with ring hydrogens substituted with radicals such as alkyl, alkoxy, or thioalkyl containing 1 to 18 carbon atoms; aryl containing 6 to 18 carbon atoms; or halogen, e.g., fluorine, chlorine, bromine, or iodine. Ar is preferably unsubstituted 1,4-phenylene or 2,6-naphthylene, and most preferably unsubstituted 1,4-phenylene.

R in the foregoing equations is an alkyl radical preferably containing 1 to 3 carbon atoms wherein the open bonded carbon atom is also bonded to a hydrogen atom, and which may be substituted with a phenyl or halide radical, e.g., fluoride, chloride, bromide or iodide. R is preferably methyl, ethyl, or n-propyl and most preferably methyl.

The amine organo groups of the contemplated thiocarbamates, i.e., R' in equations (I) to (IV), are such that the amine nitrogen atom is attached to two different carbon atoms each of which is saturated with hydrogen atoms, other carbon atoms or a combination of those, or is an aromatic ring carbon atom. The organo groups may be, for example, any of the groups identified by Newman et al, as satisfying $R_4$ and $R_5$ in Formula V shown in their U.S. Pat. No. 3,476,791, the entire disclosure of which is incorporated by reference, or such organo groups may be any of those identified herein as satisfying R and R" in equations (I) to (VIII). Preferably, R' is lower alkyl, e.g., containing 1 to 4 carbon atoms such as methyl, ethyl, n-propyl, or n-butyl, and is most preferably methyl.

R" in equations (V) to (VIII) is a radical containing, for example, 1 to 18 carbon atoms, preferably 1 to 4 carbon atoms. R" may be, for example, alkyl, alkenyl, alkynyl, alkoxyalky,, or acyloxyalkyl containing 1 to 18 carbon atoms, either unsubsiitued or substituted with radicals such as halogen, e.g., fluorine, chlorine, bromine, or iodine; acyloxy, acylamide, or an aryl radical, which may be a monovalent radical corresponding to the definition of Ar given above except that only one ring is removed to form an open valence. More preferably, R is methyl, ethyl, propyl, or n-butyl and most preferably methyl.

R''' in equations (VIII) and (IX) is a double-bonded alkylidene group having the same number of carbon atoms and carbon skeleton as R.

In equations (V) and (VII), Y is the residue minus the acyl group, R''-C=O, of compounds which are known acylating agents, such as hydroxy, acyloxy, e.g., acetoxy, and halide, e.g., fluoride, chloride or bromide. Acylating agents which may be used are for example, acyl halides, e.g., acetyl and propionyl fluorides, chlorides, and bromides, alkanoic acids, e.g., acetic and propionic acids, and alkanoic acid anhydrides, e.g., acttic and propionic anhydrides.

Preferably, the process of the invention is carried out such that, in the foregoing equations, Ar is 1,4-phenylene, R, R,' and R'' are methyl, R''' is methylidene, and Y and X are chloride, such hhat, for example -hydroxyacetophenone (4-HAP) is reacted with N,N-dimethylthiocarbamoyl chloride (DMTC) to form O-(4'-acetophenyl) N,N-dimethyl thiocarbamate (equation I), which in turn is pyrolytically rearranged to form S-(4'-acetophenyl) N,N-dimethylthiocarbamate (equation II). The latter is then reduced and hydrolyzed, e.g., with sodium borohydride and potassium hydroxide to form 4'-(1-hydroxyethyl) thiophenol (equation III), the thiol group of which is acetylated to form 4'-(1-hydroxyethyl) thiophenol acetate (equation VII). Such acetate ester is then dehydrated, e.g., using potassium acid sulfate as a dehydrating agent, to obtain para-vinylthiophenol acetate (equation VIII).

Alternatively, the S-(4'-acetophenyl) N,N-dimethylthiocarbamate is hydrolyzed and acylated with an acylating agent, e.g., acetyl chloride, to form 4'-acetothiophenol acetate (equations IV and V) which is reduced and hydrolyzed to form 4'-(1-hydroxyethyl) thiophenol (equation VI). The thiol group of the latter compound is then acylated and the resulting acetate dehydrated, as described for the previous method to obtain para-vinyl-thiophenol acetate (equations VII and VIII).

If desired, the unesterified para-vinylthiophenol may be obtained by dehydrating the 4'-(1-hydroxyethyl) thiophenol produced by either of the described methods without first acylating such compound (equation IX).

Preferably, the hydroxy aromatic ketone, e.g., 4-HAP, used as the starting compound for the reaction of equation (I) is prepared by the Fries rearrangement of an aromatic ester, e.g., phenyl acetate, or the Friedel-Crafts acylation of a phenolic compound, e.g., phenol, with an acylating agent, e.g., acetic acid or acetic anhydride, using hydrogen fluoride as catalyst, since this allows for the production of the alkenylthiophenol starting with relatively cheap and available raw materials. Conditions for these reactions are shown in the previously cited U.S. Pat. No. 4,524,217, the disclosure of which has been incorporated herein by reference. If 4-HAP is used as an intermediate in obtaining the desired product, the procedures for producing 4-HAP from phenol and acetic acid or anhydride may be used which are disclosed in pending U.S. patent applications, Ser. Nos. 714,407, filed March 21, 1985 by Davenport et al, 716,016, filed March 26, 1985 by Mott et al, and 721,007, filed April 8, 1985 by Mott, now U.S. Pat. No. 4,607,125, the entire disclosures of which are incorporated by reference. Similarly, if 6-hydroxy-2-acetonaphthone (6,2-HAN) is used as an intermediate, procedures for producing this product by the Friedel-Crafts acylation of 2-naphthol with acetic anhydride or acetic acid, and by the Fries rearrangement of 2-naphthyl acetate are shown respectively in U.S. Pat. No. 4,593,125, issued June 3, 1986 to Davenport et al, and pending application Ser. No. 870,062, filed June 3, 1986 by Davenport. The entire disclosures of the foregoing patent application are incorporated by reference.

The various reactions making up the method of this invention may be carried out using reaction conditions known in the art for the particular type of reaction involved, e.g., esterification or acylation, pyrolytic rearrangement, reduction, hydrolysis, etc., modifying the conditions so that they are suitable for the reactants being utilized. As an instance, the formation of O-(acylaryl) N,N-di(organo)thiocarbamate by the esterification reaction of equation (I) may be accomplished, for example, by contacting the hydroxy aromatic ketone, e.g., 4-HAP, with the N,N-di(organo)thiocarbamoyl halide, e.g., DMTC at a temperature of about 25 to 50° C. for a period of about 30 to 60 minutes. Preferably the reaction is carried out in the presence of a base, e.g., sodium hydroxide, potassium hydroxide, sodium hydride, or sodium methoxide. The reaction may be carried out in the presence of an appropriate solvent, e.g., one which is capable of dissolving at least part of the reactants and is inert to the reaction. Solvents which can be used are dimethyl formamide and alcohols, e.g., methanol, ethanol and t-butanol.

The pyrolytic rearrangement of the foregoing O-(acylaryl) N,N-di(organo)thiocarbamate to the S-(acylaryl) N,N-di(organo)thiocarbamate (equation II) may be accomplished by heating the O-(acylaryl) N,N-di(organo) thiocarbamate to a temperature of about 200 to 300° C. for a period of about 30 to 120 minutes. In general, the lower the temperature, the longer the period of time to effect substantially complete rearrangement of the O-aryl to the S-aryl thiocarbamate.

The reduction and hydrolysis reactions shown in equations (III) and (VI) may be accomplished, for example, by slowly adding to a cooled solution of acylthiophenol thioester, i.e., the carbamate or alkanoate, in an alcohol, e.g., methanol, ethanol, or t-butanol, a reducing agent containing available hydrogen, e.g., sodium or potassium borohydride or lithium aluminum hydride. The solution may then be warmed to room temperature and heated at reflux, e.g., for a period of about 0.5 to 3.0 hours. The solution may then be cooled, a base such as aqueous potassium or sodium hydroxide or an alkyl amine added, and again refluxed for a period of about 0.5 to 2 hours. The solution may then be diluted with water, acidified, e.g., with a dilute mineral acid to form the free thiol, and the (1-hydroxyalkyl) thiophenol product extracted with a suitable solvent such as dichloromethane.

The hydrolysis reactions of equations (III), (IV) and (VI) may be similarly carried out by refluxing an aqueous alcohol solution of the compound to be hydrolyzed and an alkali metal hydroxide (about 1 to 4 equivalents) for a period of about 0.5 to 2 hours. The resulting thiol may then be extracted from the aqueous phase with a suitable solvent, e.g., dichloromethane, after acidification with a dilute mineral acid, e.g. hydrochloric acid.

The resulting free thiol may then be acylated in accordance with equations (V) and (VII) by contacting it for a sufficient period of time with a molar excess of an acylating agent, e.g., an acid chloride such as acetyl chloride, at a relatively low temperature, e.g., about −78 to 25° C. and in the presence of a weak amine base, e.g., pyridine, which has the effect of accelerating the reaction. Alternatively, the free thiol may be acylated, for example, by contacting it with an acid anhydride, e.g., acetic anhydride, at a temperature, for example, of about 20 to 140° C, for a period, for example, of about 15 to 120 minutes either in the absence or presence of base, e.g., potassium hydroxide or sodium acetate.

The dehydration reactions of equations (VIII) and (IX) are accomplished by contacting the compound to be dehydrated with a suitable dehydrating agent or catalyst at reaction temperatures, preferably in the presence of an inhibitor of polymerization. Dehydrating agents which may be used, are, for example, hydrogensulfates, pyrosulfates, aluminates, and silicates of alkali metals, e.g., sodium and potassium, alkaline earth metals, e.g., calcium and magnesium, and transition metals, e.g., tungsten. When such a dehydrating agent is used, it may be present in an amount of about 0.1 to 50, preferably about 1 to 20 wt.%, based on the weight of the composition. The dehydration may be carried out in the liquid phase, for example, at a temperature in the range of about 100 to 250° C., preferably about 160 to 180° C. under a reduced pressure in the range of about 0.1 to 20 mm HgA, preferably about 1 to 2 mm HgA.

Inhibitors which may be present during dehydration with a dehydrating agent of the type described are, for example, t-butylcatechol, hydroquinone, m-dinitrobenzene, N-nitrosodiphenylamine, picric acid, sodium sulfite, quinhydrone and the like. The inhibitor may be present in an amount, for example, of about 0.001 to 30, preferably about 0.1 to 15 wt.%, based on the weight of the composition.

If desired, the dehydration reaction may be carried out in the presence of a non-volatile solvent such as sulfolane or diphenyl ether.

It is also possible to carry out the dehydration in the vapor phase over a heterogeneous dehydration catalyst, particularly if the compound being dehydrated is an unacylated (1-hydroxyalkyl) thiophenol such as 4'-(1-hydroxyethyl) thiophenol. Catalysts which may be used are, for example, alumina, and the temperature of reaction may be, for example, 200 to 400° C., preferably 250 to 300° C. In this case, the alkenylthiophenol product is preferably condensed and distilled in the presence of one of the foregoing polymerization inhibitors, preferably under reduced pressure within the ranges given previously for dehydration in the liquid phase.

DESCRIPTION OF SPECIFIC EMBODIMENTS

The following examples further illustrate the invention.

Example 1 illustrates the formation of O-(4'-acetophenyl) N,N-dimethylthiocarbamate by reaction of 4-hydroxyacetophenone with N,N-dimethylthiocarbamoyl chloride (DMTC) in accordance with equation (I) wherein Ar is 1,4-phenylene, and R and R' are methyl.

EXAMPLE 1

A 5 liter flask equipped with a mechanical stirrer was charged with KOH (123 g, 2.2 mol) and methanol (500 mL). The solution was cooled in ice, 4-hydroxyacetophenone (272 g, 2.0 mol) added and the reaction mixture stirred for 0.25 h. N,N-Dimethylthiocarbamoyl chloride (274 g, 2.2 mol) was added and the reaction mixture gradually warmed to room temperature. An exothermic reaction was observed and a solid precipitated. After stirring the reaction mixture for an additioaal 0.5 h, water (3 L) was added. The contents of the flask were cooled in ice, and the ensuing precipitate was collected via filtration and washed with water. Drying of the solid in vacuo (150 mm HgA) at 50° C. afforded 382 g (85.7% yield) of O-(4'acetophenyl) N,N-dimethylthiocarbamate. The product was 97% pure by high performance liquid chromatography (HPLC).

Example 2 illustrates the formation of S-(4'-acetophenyl) N,N-dimethylthiocarbamate by the pyrolytic rearrangement of O-(4'-acetophenyl) N,N-dimethylthiocarbamate in accordance with equation (II) where Ar is 1,4-phenylene and R and R' are methyl.

EXAMPLE 2

O-(4'-Acetophenyl) N,N-dimethylthiocarbamate (300 g, 1.35 mol) was heated under an inert atmosphere at 220° C. for 1 h. A water:methanol mixture (5:1, 600 mL) was added with stirring while the flask was hot causing a yellow solid to precipitate. The solid was filtered and washed with water. Drying of the solid in vacuo (150 mm HgA) at 50° C. afforded S-(4'acetophenyl) N,N-dimethylthiocarbamate (291.5 g, 97.2% yield). HPLC analysis showed complete conversion to the product.

Example 3 illustrates the formation of 4'-(1-hydroxyethyl) thiophenol by the reduction and hydrolysis of S-(4'-acetophenyl) N,N-dimethylthiocarbamate in accordance with equation (III) where Ar is 1,4-pheylene and R and R' are methyl.

EXAMPLE 3

S-(4'-Acetophenyl) N,N-dimethylthiocarbamate (8.0 g, 0.036 mol) was dissolved in absolute alcohol (80 mL) and cooled in ice. Sodium borohydride (3.0 g, 0.08 mol) was added slowly. The reaction mixture was warmed to room temperature, heated at reflux for 1 h, cooled and 40% potassium hydroxide (20 mL) added. The reaction mixture was heated at reflux for an additional 2 h, cooled, and washed with dichloromethane (75 mL). The organic layer was discarded, the aqueous layer was carefully acidified with dilute hydrochloric acid, and the product was extracted in dichloromethane (2×75 mL). The combined dichloromethane extract was washed with water (75 mL), separated, dried, and concentrated in vacuo to afford an oil which solidified on cooling (6.0 g) in quantitative yield of 4'-(1-hydroxyethyl) thiophenol.

Example 4 illustrates the formation of 4'-acetothiophenol acetate by the hydrolysis and acetylation of S-(4'-acetophenyl) N,N-dimethylthiocarbamate in accordance with equations (IV) and (V), where Ar is 1,4-phenylene, R, R' and R" are each methyl and Y is chloride.

EXAMPLE 4

S-(4'-Acetophenyl) N,N-dimethylthiocarbamate (43.0 g, 0.19 mol) was added to a solution of potassium hydroxide (12.3 g, 0.22 mol) in ethylene glycol:water (3:1, 80 mL). The reaction mixture was heated at reflux for 1 h, and cooled; water (100 mL) was added and the resulting aqueous phase was washed with dichloromethane (50 mL). The aqueous phase was carefully acidified with dilute hydrochloric acid. The product was extracted in dichloromethane (2×100 mL) and dried; to this solution acetyl chloride (23.6 g, 0.3 mol) was added. The reaction mixture was cooled to −78° C and pyridine (23.7 g, 0.3 mol) was added dropwise. The reaction mixture was warmed to room temperature and washed with ice-water (2×100 mL). The organic layer was separated, dried, and concentrated to afford the product (32.6 g, 87.1% yield).

Example 5 illustrates the formation of 4'-(1-hydroxyethyl) thiophenol acetate by the reduction and hydrolysis of 4'-acetothiophenol acetate in accordance with equation (VI) where Ar is 1,4-phenylene and R and R" are methyl.

EXAMPLE 5

4-Acetothiophenol acetate (19.4 g, 0.1 mol) was dissolved in absolute alcohol (50 mL) and cooled in ice. Sodium borohydride (5.7 g, 0.15 mol) was added slowly while maintaining the reaction temperature below 25° C. After the addition of sodium borohydride was complete, the reaction mixture was stirred for an additional 1 h and cooled in ice. Potassium hydroxide (12 g) was added slowly with stirring. The reaction mixture was diluted with water (200 mL), carefully acidified with dilute hydrochloric acid, and the product was extracted into dichloromethane (2×75 mL). The organic layer was separated, dried, and concentrated in vacuo to afford the product (12.0 g, 77.9% yield).

Example 6 illustrates the formation of 4'-(1-hydroxyethyl) thiophenol acetate by the acetylation of 4'-(1-hydroxyethyl) thiophenol in accordance with equation (VII) where Ar is 1,4-phenylene, R and R" are methyl and Y is chloride.

EXAMPLE 6

4'-(1-Hydroxyethyl) thiophenol (12.0 g, 0.078 mol) was dissolved in dichloromethane (75 mL) and cooled in ice. Acetyl chloride (6.12 g, 0.078 mol) was added and the reaction mixture was stirred for 5 min. Pyridine (6.32 g, 0.08 mol) was added dropwise and the reaction mixture was stirred for 0.25 h. The reaction mixture was washed with ice-water, separated, dried, and concentrated to afford the product (14.9 g, 97.4% yield).

Example 7 illustrates the formation of para-vinylthiophenol acetate by the dehydration of 4'-(1-hydroxyethyl) thiophenol acetate in accordance with equation (VIII) where Ar is 1,4-phenylene, R and R" are methyl, and R'" is methylidene.

EXAMPLE 7

4'-(1-Hydroxyethyl) thiophenol acetate (14.0 g, 0.071 mol) was mixed with potassium bisulfate (1.4 g) and t-butyl catechol (0.8 g) in a round bottomed flask equipped with a short vigreux column and a distillation head. The flask was evacuated (2 mm HgA) and heated to 160°–180° C. The product was distilled as a colorless liquid (2.5 g, 19.8% yield): b.p. 110° C.

Example 8 illustrates the formation of O-(6-acetyl-2-naphthyl) N,-dimethylthiocarbamate by reaction of 6-hydroxy-2-acetonaphthone with N,N-dimethylthiocarbamoyl chloride (DMTC) in accordance with equation (I), wherein Ar is 2,6-naphthylene, R and R' are methyl and X is chloride.

EXAMPLE 8

6-Hydroxy-2-acetonaphthone (18.6 g, 0.1 mol) was added to an ice cooled solution of potassium hydroxide (6.84 g, 0.12 mol) in methanol (100 mL). The solution was stirred for 0.25 h, N,N-dimethylthiocarbamoyl chloride (14.83 g, 0.12 mol) was added and the reaction mixture was stirred for 0.5 h. Water (150 mL) was added and the solid filtered and washed with water. Drying of the solid in vacuo (150 mm HgA) at 50° C. afforded O-(6-acetyl-2-naphthyl-N,N-dimethylthiocarbamate (27.3 g, 81.7% yield). The product was found to be 97.4 % pure by HPLC. $^1$H NMR (CDCl$_3$):δ 8.43 (s, 1H), 8.05–7.81 (m, 3H), 7.53 (s, 1H) 7.35–7.27 (m, 1H), 3.47 (s, 3H), 3.39 (s, 3H), and 2.70 (s, 3H); $^{13}C$ NMR (CDCl$_3$):δ 197.63, 187.34, 135.53, 135.99, 134.39, 130.46, 129.83, 128.07, 124.46, 123.53, 119.48, 43.19, 38.72, and 26.50 ppm.

Example 9 illustrates the formation of S-(6-acetyl-2-naphthyl)-N,N-dimethylthiocarbamate by the pyrolytic rearrangement of O-(6-acetyl-2-naphthyl) N,N-dimethylthiocarbamate inaccordance with equation (II), where Ar is 2,6-naphthylene and R and R' are methyl.

EXAMPLE 9

O-(6-acetyl-2-naphthyl) N,N-dimethylthiocarbamate (10 g, 0.037 mol) was heated at 220° C. for 2 h under an inert atmosphere. After cooling, the reaction product was dissolved in methanol (100 mL) and water (100 mL) was added. A solid precipitated which was collected via filtration, and dried in vacuo (150 mm HgA) at 50° C. to afford the S-(6-acetyl-2-naphthyl) N,N-dimethylthiocarbamate (9.6 g, 96% yield). HPLC analysis showed 96% conversion to the product. $^1$H NMR (CDCl$_3$): δ8.44 (s, 1H), 8.06–7.83 (m, 4H), 7.65–7.60 (m, 1H), 3.09 (br s, 6H), and 2.71 (s, 3H); $^{13}C$ NMR (CDCl$_3$): δ197.66, 166.21, 135.49, 135.31, 134.57, 132.77, 132.32, 129.66, 128.35, 124.40, 36.90, and 26.54 ppm.

Using the procedures of Examples 3, 6 and 7,S-(6-acetyl-2-naphthyl) N,N-dimethylthiocarbamate may be reduced and hydrolyzed to 6'-(1-hydroxyethyl)-2'-thionaphthol which may in turn be acetylated to 6'-(1-hydroxyethyl)-2'-thionaphthol acetate, and the latter compound may be dehydrated to 6-vinyl-2-thionaphthol acetate, in accordance with equations (III), (VII) and (VIII). Alternatively, using the procedures of Examples 4, 5 and 7, the S-(6-acetyl-2-naphthyl) N,N-dimethylthiocarbamate may be hydrolyzed and acetylated to 6-aceto-2-thionaphthol acetate which may be reduced and hydrolyzed to 6'-(1-hydroxyethyl)-2'-thionaphthol acetate and the latter compound dehydrated to 6-vinyl-2-thionaphthol acetate, in accordance with equations (IV), (V), (VI) and (VIII). In all the equations for this series of reactions, Ar is 2,6-naphthylene, R, R' and R" ar each methyl, R'" is methylidene, and Y is chloride.

We claim:

1. A method for producing alkenylthiophenols and their esters comprising reacting a hydroxy aromatic ketone with an N,N-di(organo)thiocarbamoyl halide to form an O-(acylaryl) N,N-di(organo)thiocarbamate, pyrolytically rearranging the latter compound to form an S-(acylaryl) N,N-di(organo)thiocarbamate, and either (I) reducing the S-(acylaryl) N,N-di(organo)thiocarbamate to form an S-(1-hydroxyalkylaryl) N,N-di(organo)thiocarbamate which is then either a) hydrolyzed to form a (1-hydroxyalkyl) thiophenol, or b) dehydrated to form an S-(alkenylaryl) N,N-di(organo)thiocarbamate which is then hydrolyzed to form an alkenylthiophenol; or alternatively, (II) hydrolyzing said S-(acylaryl) N,N-di(organo)thiocarbamate to form an acylaryl thiophenol, acylating the thiol group of the latter compound to form an acylthiophenol thioester, and reducing and hydrolyzing said acylthiophenol ester to form a (1-hydroxyalkyl) thiophenol; and then either dehydrating said (1-hydroxyalkyl) thiophenol made by any of the foregoing methods to form an alkenylthiophenol or acylating the thiol group of said (1-hydroxyalkyl) thiophenol and dehydrating the resulting thioester to form an groups being at the ring-bonded carbon atoms, the organo groups in said thiocarbamates being such that the amino nitrogen is attached to two different carbon atoms each of which is saturated with hydrogen atoms, other carbon atoms, or a combination of those, or is an aromatic ring carbon atom.

2. The method of claim 1 wherein said organo groups are lower alkyl.

3. The method of claim 1 wherein said S-(acylaryl) N,N-di(organo)thiocarbamate is reduced and hydrolyzed to form a (1-hydroxyalkyl) thiophenol, the thiol group of which is acylated, and the resulting thioester is dehydrated to form an alkenylthiophenol thioester.

4. The method of claim 1 wherein said S-(acylaryl) N,N-di(organo)thiocarbamate is hydrolyzed to form an acylthiophenol which is acylated, the resulting thioester is reduced and hydrolyzed to form a (1-hydroxyalkyl) thiophenol, the latter compound is acylated to form a (1-hydroxyalkyl) thiophenol ester, and the latter thioester is dehydrated to form an alkenylthiophenol acylate.

5. The method of claim 1 wherein said hydroxy aromatic ketone is prepared by contacting an ester of phenolic compound and a carboxylic acid with a Fries rearrangement catalyst at an elevated temperature.

6. The method of claim 1 wherein said hydroxy aromatic ketone is prepared by contacting a phenolic compound and an acylating agent with a Friedel-Crafts catalyst at an elevaed temperature.

7. The method of claim 1 wherein said reducing is carried out in the presence of an alkali metal borohydride or lithium aluminum hydride as reducing agent.

8. A method for producing para-vinylthiophenol acetate comprising reacting 4-hydroxyacetophenone with N,N-dimethylthiocarbamoyl chlorid,, to form O-(4'acetophenyl) N,N-dimethylthiocarbamate, pyrolytically rearranging the latter compound to form S-(4'-acetophenyl) N,N-dimethylthiocarbamate, reducing and hydrolyzing the latter compound to form 4'-(1-hydroxyethyl) thiophenol, acetylating the thiol group of the latter compound, and dehydrating the resulting 4'-(1-hydroxyethyl) thiophenol acetate to form said para-vinylthiophenol acetate.

9. The method of claim 8 wherein said 4-hydroxyacetophenone is prepared by contacting phenyl acetate with hydrogen fluoride as a Fries rearrangement catalyst, at an elevated temperature.

10. The method of claim 8 wherein said 4-hydroxyacethophenone is prepared by contacting phenol and acetic anhydride or acetic acid with hydrogen fluoride as a Friedel-Crafts catalyst, at an elevated temperature.

11. The method of claim 8 wherein said reducing is carried out in the presence of sodium borohydride as reducing agent.

12. A method for producing para-vinylthiophenol acetate comprising reacting 4-hydroxyacetophenone with N,N-dimethylthiocarbamoyl chloride, to form O-(4'acetophenyl) N,N-dimethylthiocarbamate, pyrolytically rearranging the latter compound to form S-(4'acetophenyl) N,N-dimethylthiocarbamate, hydrolyzing the latter compound to form 4-acetothiophenol, acetylating the thiol group of said 4-acetothiophenol to form its acetate, reducing and hydrolyzing the latter acetate to form 4'-(1-hydroxyethyl) thiophenol, acetylating the thiol group of the latter compound, and dehydrating the resulting 4'-(1-hydroxyethyl) thiophenol acetate to form para-vinylthiophenol acetate.

13. The method of claim 12 wherein said 4-hydroxyacetophenone is prepared by contacting phenyl acetate wtih hydrogen fluoride as a Fries rearrangement catalyst, at an elevated temperature.

14. The method of claim 12 wherein said 4-hydroxyacetophenone is prepared by contacting phenol and acetic anhydride or acetic acid with hydrogen fluoride as a Friedel-Crafts catalyst, at an elevated temperature.

15. The method of claim 12 wherein said reducing is carried out in the presence of sodium borohydride as reducing agent.

* * * * *

UNITED STATES PATENT AND TRADEMARK OFFICE
CERTIFICATE OF CORRECTION

PATENT NO. : 4,794,205
DATED : December 27, 1988
INVENTOR(S) : Mohammad Aslam, Kenneth G. Davenport, Russell R. Graham It is certified that error appears in the above—identified patent and that said Letters Patent is hereby corrected as shown below:

ON THE TITLE PAGE, Item [75] should read

-- Inventors: Mohammad Aslam, Kenneth G. Davenport and
Russell R. Graham, all of Corpus Christi, Texas. --.

Signed and Sealed this

Seventh Day of November, 1989

*Attest:*

JEFFREY M. SAMUELS

*Attesting Officer*     *Acting Commissioner of Patents and Trademarks*